United States Patent
Alander et al.

(10) Patent No.: US 6,552,208 B1
(45) Date of Patent: Apr. 22, 2003

(54) FRACTIONATION PROCESS

(75) Inventors: Jari Alander, Karlshamn (SE); Ann-Charlotte Andersson, Karlshamn (SE); Håkan Malmros, Karlshamn (SE); Jörgen Nilsson, Asarum (SE)

(73) Assignee: Karlshamns AB, Karlshamn (SE)

( * ) Notice: Subject to any disclaimer, the term of this patent is extended or adjusted under 35 U.S.C. 154(b) by 0 days.

(21) Appl. No.: 09/701,392

(22) PCT Filed: Jun. 1, 1999

(86) PCT No.: PCT/SE99/00945
§ 371 (c)(1),
(2), (4) Date: Jan. 18, 2001

(87) PCT Pub. No.: WO99/63031
PCT Pub. Date: Dec. 9, 1999

(30) Foreign Application Priority Data

Jun. 2, 1998 (SE) ................................................ 9801955

(51) Int. Cl.⁷ .................................................. U11B 7/00
(52) U.S. Cl. .......................... 554/208; 554/8; 554/206; 554/211; 426/417
(58) Field of Search ............................ 554/8, 206, 208, 554/211; 426/417

(56) References Cited

U.S. PATENT DOCUMENTS

| 2,972,541 A | | 2/1961 | Cochran et al. | |
|---|---|---|---|---|
| 5,427,790 A | * | 6/1995 | Frische et al. | 426/195.1 |
| 5,679,393 A | * | 10/1997 | Laur et al. | 426/417 |

FOREIGN PATENT DOCUMENTS

| EP | 0 081 881 | 6/1983 |
|---|---|---|
| GB | 2 177 715 | 1/1987 |
| WO | WO 92/22626 | 12/1992 |
| WO | WO 96/38047 | 12/1996 |

OTHER PUBLICATIONS

Derwent Publications, AN 83–738546, JP 58–116415, Jul. 11, 1983.

Derwent Publications, AN 85–259334, JP 60–172257, Sep. 5, 1985.

Derwent Publications, AN 1977–57116, JP 51–119706, Oct. 20, 1976.

* cited by examiner

*Primary Examiner*—Deborah D. Carr
(74) *Attorney, Agent, or Firm*—Oblon, Spivak, McClelland, Maier & Neustadt, P.C.

(57) ABSTRACT

The invention refers to a process for fractionating a vegetable oil giving one or more solid fractions suitable for confectionary applications as well as a liquid fraction rich in unsaponifiable biologically active components. The liquid fractions of shea butter and rapeseed oil having a high content of phytosterols and tocoferols, respectively, are useful for cosmetical and pharmaceutical preparations.

24 Claims, No Drawings

FRACTIONATION PROCESS

This application is a 971 of PCT/SE99/00945 filed Jun. 1, 1999.

The present invention refers to a new process for fractionation of vegetable oils giving a confectionary fat as well as a product enriched in unsaponifiable components.

BACKGROUND OF THE INVENTION

In the fractionation of vegetable oils to obtain a main fraction suitable for the manufacture of confectionary fats different liquid side fractions are also obtained. Said side fractions, the composition of which varies with the starting oil and the fractionation conditions, have been used in the food industry, for example for the preparation of emulsifiers, but are in general regarded as of little value.

It is well known that vegetable oils and fats contain a large number of biologically active components in addition to the dominating triglycerides. Such components are for instance polar lipids, that is phospholipids, sphingolipids and galactolipids, as well as more or less nonpolar lipid components such as phytosterols, triterpene alcohols and aliphatic alcohols, tocopherols, vitamin E for instance, and tocotrienols. The unsaponifiable part of the oil, by definition the material from a lipid sample which can be extracted by petroleum ether or diethyl ether after alkaline hydrolysis, is typically said to comprise said nonpolar to semi-polar lipids, hydrocarbons and waxes.

The unsaponifiable components of many vegetable oils are known to have different properties of interest for use in cosmetic and pharmaceutical preparations (Wachter, R., et al., Phytosterole—pflanzliche Wirkstoffe in der Kosmetik, Parfümerie und Kosmetik, 75. Jahrgang, Nr. 11/94). The natural content and composition of the unsaponifiable lipid components in vegetable oils is unique for each raw material. The functionality of different concentrates enriched in unsaponifiable product is explained by the respective composition of said components, mainly tocopherols, phytosterols and triterpene esters.

Shea butter, for instance, has an unusually high content of unsaponifiable matter, up to 13%, hydrocarbons inclusive. The unsaponifiable lipids of shea butter are characterized by a high content of UV-absorbing triterpene esters and natural phytosterols claimed to impose anti-inflammatory effects on damaged skin.

The unsaponifiable lipids of rapeseed oil are dominated by a unique high content of sterols, such as β-sitosterol, campesterol and brassicasterol, as well as tocopherols known to offer a good natural protection against oxidation. An unsaponifiable fraction of rapeseed oil has proven to show an anti-inflammatory effect on irritated skin (Lodén, M., et al., Effect of topically applied lipids on surfactant-irritated skin, British Journal of Dermatology 1996; 134: 215–220).

In the manufacturing of raw material for the food industry many of the unsaponifiable components in the vegetable fat or oil are negatively affected by the processing conditions and others are removed. The content of unsaponifiable components varies with the origin of the raw material. Typically the non glyceride part of a refined oil amounts to 0.5–1.0% by weight.

In order to obtain the unsaponifiable, biologically active components of interest there are different ways to proceed. The oil can for instance be saponified and components of interest extracted, which process will however produce large amounts of fatty acids and glycerol. In addition some of the components, for instance esters of sterols and triterpene alcohols will become saponified and lose their oil solubility. Another method is steam distillation of the oil and processing of the distillate. In this method the oil is under low pressure blown with steam which takes away volatile components, more or less, depending on the pressure and the temperature. However, also triglycerides and fatty acids are taken away and the distillate has to be subjected to a saponification and extraction procedure, alternatively to a short path distillation, in order to purify the components of interest. By this the activity and quality of the components are reduced. Still another method is to fractionate the oil in a suitable solvent at a low temperature. This is a preferred process as the active components can be obtained or concentrated without being chemically modified.

PRIOR ART

Processes for fractionating oils and fats have since long been used for the manufacturing of confectionary fats or hard butters and also for obtaining fractions having certain specific characteristics. The liquid products which are obtained as by-products have been used in the food industry. In the processing of a vegetable oil one or more of the following steps are normally used:

pressing or extraction of the raw material;

refining of the pressed or extracted oil, that is degumming with acid to remove the polar lipids, deacidification with alkali to remove free fatty acids, and bleaching to reduce colour and oxidation products;

catalytic hydrogenation;

solvent fractionation of the hydrogenated oil bringing the triglycerides to precipitate;

deodorization by means of steam to remove components that give rise to unwanted flavours and odours.

U.S. Pat. No. 2,972,541, for instance, refers to hard butters and a method for preparing said hard butters by solvent fractionation from oils composed of essentially triglycerides of fatty acids of 16 and 18 carbon atoms. In order to recover triglycerides of interest the starting oil is hydrogenated to convert the fatty acid radicals of the oil from cis to trans figuration and to lower the initial unsaturation by eliminating most of the polyethenoic unsaturation. The hydrogenated oil can then be solvent fractionated, a technique well known in the glyceride oil art, to give a crystalline hard butter fraction. Nothing is, however, stated about the unsaponifiable fraction or the content of non-triglycerides in the oil.

EP-B1-0690904 refers to a process for the preparation of fractions of a fat of vegetable origin enriched with unsaponifiable materials, which process is characterized in that the fat is treated with a polar solvent such as acetone and heated giving a first fraction insoluble in hot solvent which is rich in unsaponifiable material. Said first fraction can be combined with a second fraction obtained from the soluble fraction after crystallization thereof at a temperature below 0° C., preferably at −15 to −30° C., filtration and evaporation of the filtrate. The obtained fraction enriched in unsaponifiable material is said to be useful for the preparation of cosmetical and pharmaceutical compositions, but nothing is stated about the utility of the solid fractions. The fat described is shea butter.

WO 96/03137 refers to cosmetic and pharmaceutical preparations containing shea butter concentrates having an increased content of components which can not be saponified. Said shea concentrates have been produced from raw or refined shea butter by distillation in a short path distiller at a temperature of 200–300° C. and at a reduced pressure. It is also said to be possible to produce adequate concentrates by extraction of shea butter with organic solvents such as ethanol. In this process the original composition of the unsaponifiable components will, however, be destroyed as the esters are hydrolysed, oxidised and/or isomerised.

There is still a need of a process from which it will be possible to obtain, in addition to one or more hard fractions suitable for confectionary applications, a useful side fraction, such as a liquid fraction rich in chemically unaltered, unsaponifiable, biologically active components from vegetable oils in a cost effective way.

DESCRIPTION OF THE INVENTION

The present invention refers to a process for fractionation of a vegetable oil in order to obtain one or more steeply melting solid fractions suitable for confectionary applications as well as a liquid fraction rich in unsaponifiable, biologically active components.

In order to prepare confectionary fats, as well as a fraction rich in unsaponifiable, biologically active components, from a vegetable oil the oily raw material should be treated by the following steps in any suitable order: —pretreatment, that is pressing or extraction of the oil, refining, that is degumming with acid, deacidification and bleaching;

optional catalytic hydrogenation;

fractionation; and after-treatment.

The invention refers to a process for fractionation of a vegetable oil giving one or more solid fractions suitable for confectionary applications a well as a liquid fraction rich in unsaponifiable, biologically active components, wherein an optionally pretreated oil having a melting point of 32–55° C. is mixed with solvent in a ratio of 1:3–7 (w/v), heated to transparency, and then cooled at a rate of 0.1–1.5° C./min and filtrated in one or more steps to a first fractionation temperature of –5 to +10° C., at which temperature one or more precipitated solid fractions suitable for use in confectionary applications have been filtered off giving a filtrate F1, characterised in that a) the filtrate F1 optionally is mixed with additional solvent;

b) the filtrate F1 is cooled at a rate of 0.1–1.0° C./min to a second fractionating temperature of –30 to –15° C., at which temperature the precipitated solid -fraction is filtered off giving a filtrate F2;

c) the filtrate F2 is distilled to remove the solvent giving a liquid fraction in which the unsaponifiable, biologically active components have been enriched by at least a factor 2.

It has surprisingly been found that a repeated fractionation at a low temperature as described above will bring about an enrichment of the unsaponifiable components of a vegetable oil in the final liquid phase to an extent far superior to what could be expected. This must be ascribed to the fact that the desired, unsaponifiable components in spite of high melting points surprisingly are soluble in the liquid triglycerides present in the vegetable oils also at very low temperatures and therefore can be enriched to a higher than expected level of concentration.

Cocoa butter alternatives, CBA, are usually divided into 3 categories, that is Cocoa Butter Equivalents, CBE, Cocoa Butter Replacers, CBR, and Cocoa Butter Substitutes, CBS, depending on their compatibility and structural similarity to cocoa butter. Cocoa butter equivalents are characterised by a triglyceride composition dominated by the same combinations of stearic, oleic and palmitic acid based triglycerides that are found in cocoa butter (SOS, POS, and POP, where S stands for stearic, O for oleic and P for palmitic and the three letter combination defines a triglyceride). The crystallisation behaviour of these fats is also identical to that of cocoa butter. CBE's are manufactured from fats like shea butter, illipe butter, mango kernel oil, sal butter, madhuca butter and other similar fats, alone or in combination with fractionated palm oils.

Cocoa butter replacers, CBR, are used in combination with 5–35% cocoa butter in confectionary products. The chemical composition of CBRs is dominated by combinations of oleic, elaidic, stearic and palmitic acids in the triglycerides (PEP, PEO, and SEE, where E stands for elaidic acid) with a lower degree of compatibility with the cocoa butter tri-glycerides. CBRs do not need the characteristic tempering procedure necessary to obtain the correct crystal form in cocoa butter. CBRs are obtained by hydrogenating and optionally fractionating poly- and monounsaturated oils like soybean oil, cottonseed oil, rapeseed oil and groundnut oil.

Cocoa butter substitutes, CBS, have a triglyceride structure derived from shorter fatty acids (lauric and myristic) and are thus completely incompatible with cocoa butter. They are mainly derived from palm kernel oil and coconut oil by combinations of fractionation and hydrogenation.

The solid fractions obtained by the process of the invention can be used to formulate cocoa butter equivalents and cocoa butter replacers according to the description above. For example the solid fraction obtained from shea nut oil at the second fractionation temperature can be used to formulate a CBE composition, especially if combined with the solid fraction obtained at the first fractionation temperature. These high melting fractions are also characterised by a low content of unsaponifiable matter, especially triterpene alcohol esters, which improves the tempering properties and the compatibility with cocoa butter. If a hydrogenated rapeseed oil is used as starting material for the fractionation a CBR type of product can be obtained by combination of the solid fractions filtrated at the first and the second fractionation temperatures.

Vegetable oils useful as raw materials are those oils which contain the active components in an amount that can be concentrated. Examples of raw materials containing lipids that can be enriched by the process of the invention are the following: rapeseed oil (Brassica napus, rapa, campestris etc), crambe oil (Crambe abyssinica, hispanica), mustard seed oil (Brassica alba, hirta, nigra, juncea, carinata), soybean oil (Glycine max), sunflower oil (Helianthus annuus), cottonseed oil (Gossypium hirsutum, barbadense, herbaceum), peanut (or groundnut, or arachis) oil (Arachis hypogaea), linseed oil (Linus usitatissimum), evening primrose oil (Oenothera biennis, larmarkiana), borage oil (Borago officinalis), grapeseed oil (Vitis vinifera), safflower oil (Carthamus tinctorius), sesame oil (Sesamum indicum, orientale), tea seed oil (Thea sasanqua, Camellia sasanqua), corn (or maize) oil, corn fibre oil, corn bran oil (Zea mays), wheat oil, wheat bran oil or wheat germ oil (Triticum aestivum), oat oil, oat bran oil (Avena sativa), rice bran oil, rice oil (oryza sativa), olive oil (Olea europea), palm oil, palm kernel oil (Elaeis guineensis, oleifera), coconut oil (Cocos nucifera), babassu oil (orbignya martiana, oleifera), illipe butter, Borneo tallow (Shorea stenoptera), shea butter or shea oil (Butyrospermum parkii), madhuca, mowrah butter (Madhuca latifolia, indica, longifolia), sal butter (Shorea robusta), mango seed oil (Mangifera indica), avocado oil, avocado seed oil (Persea americana), cocoa butter (Theobroma cacao), hazelnut oil (Corylus avellana), almond oil (Prunus amygdala), macadamia nut oil (Macadamia tetraphylla), walnut oil (Juglans nigra), and chestnut oil (Castanea mollissima).

Preferred examples of such oils are shea butter or shea oil, rapeseed oil, canola oil, olive oil, avocado oil, peanut oil, corn oil, soybean oil, sunflower oil, hybrid sunflower oil, wheat-germ oil, illipe butter, mango kernel oil, shorea butter, sal butter, sesame oil, rice bran oil, safflower oil, linseed oil, palm oil, palm kernel oil, coconut oil, cocoa butter, cottonseed oil, oat oil, oat bran oil, as well as mixtures thereof. The oils having a naturally high content of the active components are preferred.

Unsaponifiable, biologically active components which can be enriched by the process of the invention include the following compounds of interest: retinol and acyl retinols; luteol and luteol esters; β-carotene and other carotenoids; tocopherols and tocotrienols; phytosterols, such as 4,4-dimethyl sterols (triterpene alcohols), 4-monomethylsterols, 4-de(s)methylsterols and their esters with fatty acids, cinnamic acid, substituted cinnamic acids, benzoic acid, substituted benzoic acids; avenanthramide; oil soluble flavonoids; oil soluble vitamins and vitamin precursors (Vitamin D and A); ubiquinone, phylloquinones, menaquinones and oil soluble derivatives thereof. Sterols of interest are for example β-sitosterol, stigmasterol, avenasterol, campesterol, brassicasterol, dihydrobrassicasterol, their ring saturated counter-parts (stanols) and esters with long chain saturated or unsaturated fatty acids. short chain carboxylic acids and aromatic acids. Triterpene alcohols include for example β- and β-amyrin, lupeol, parkeol, germanicol, taraxasterol, taraxerol, ψ-taraxasterol, butyrospermol, lanosterol, cycloartenol, cyclobranol, their ring saturated counterparts and esters with long chain unsaturated and saturated fatty acids, short chain carboxylic acids and aromatic acids, that is cinnamic, ferulic, caffeic, sinapic, benzoic and similar acids.

Depending on the lipid of interest and the intended functionality of the concentrate different raw materials and raw material combinations can be used. The following examples are given to illustrate the possibilities: Tocopherols are found, for example, in most polyunsaturated oils like rapeseed oil, soybean oil, corn oil, groundnut oil and sunflower oil. Tocotrienols are, for example, found in oils derived from the oil palm (Elaeis sp). Triterpene alcohols (4,4-dimethyl sterols) are found in, for example, shea butter, olive oil, rice bran oil. 4-monomethylsterols and 4-demethylsterols are common in all vegetable oils and fats, either as free sterols or esterified to fatty acids or phenolic acids.

The oil obtained from the pressing or extraction is refined carefully to preserve the active components intact. This is best done by conventional chemical refining, that is alkalic refining. The crude oil is degummed by means of phosphoric acid or citric acid, is deacidified with an aqueous solution of sodium, potassium or calcium hydroxide, and finally bleached with bentonite or silicagel. Said processes take place at a temperature of 50–90° C.

When fats or oils having a high content of unsaturated components are used as raw material it is preferable in order to obtain the characteristic, effective separation of the active components to reduce the solubility of the triglycerides by catalytic hydrogenation. Hydrogenation of vegetable oils suitable for fractionation is done using commercial Ni-containing catalysts such as Pricat 9900, Pricat 9910, Pricat 9908 and Pricat 9918 from Unichema, Nysosel 325, Nysosel 545, Nysosel 645, Nysosel 222, Nysel SP 7 and Nysel SP10 from Engelhard or G111, G95-D and KE/KTR from Sud-Chemie. It is also possible to use Pd or Pt on a carbon carrier (Pd/C or Pt/C). The hydrogenation is normally carried out using 0.005–0.15% Ni in oil at 180–220° C. and a partial pressure of hydrogen of 1.0–4.0 bar.

The hydrogenation is allowed to proceed to a melting point of 32–55° C., which implies that most of the unsaturated triglycerides have become sufficiently saturated to be solid, which makes it possible to have them removed in the solid phase in the subsequent fractionation step.

According to another aspect the invention refers to a process for fractionation of a vegetable oil or a fraction thereof comprising the additional step of catalytically hydrogenating the oil or a liquid fraction thereof in order to increase the melting point to a value within the range of 32–55° C.

If the melting point of the oil is more than 55° C., the amount of liquid to solubilise the desired components will be too small and they will be precipitating together with the solid triglycerides. The recovery of the small amount of the liquid fraction will also be more difficult than if a lower melting point is used. However, if the melting point of the starting material is too low, that is below 32° C., the concentration of the desired lipids in the liquid fraction will be too low and the desired enrichments cannot be achieved.

When the raw material oil or fat contains a large amount of saturated fats, such as shea butter, cacao butter or illipe butter, this hydrogenation step is optional, but a higher melting point of the oil will give a higher enrichment of the product.

If the vegetable oil used as a starting oil has a melting point of 38–55° C. the second fractionation temperature can be as high as −5° C., but if, on the other hand, the melting point of the oil is as low as 32–40° C. the second fractionation temperature must be lower, that is from −30 to −15° C.

The fractionation is performed by mixing the oil with a semipolar solvent, such as a ketone, for example acetone or methylethyl ketone, methylisobutyl ketone, diethyl ketone, 2-nitropropane, tetrahydrofuran or ethyl acetate, a nonpolar solvent, such as hexane or petroleum ether, or a polar solvent, such as an alcohol, such as isopropanol, ethanol or methanol, into a slurry which is cooled in a controlled way to a first fractionation temperature, generally above 0° C., preferably at about −5° C. to +10° C., at which temperature part of the fat, especially the hydrogenated or saturated triglycerides are being precipitated as one or more solid fractions. Said fractions are filtrated and the filtrate containing a liquid fraction enriched in biologically active components saved.

In a second step this filtrate is fractionated once more at a second, still lower fractionation temperature, about −15 to −30° C., at which temperature another solid phase is precipitated giving a filtrate containing a liquid fraction of a still higher concentration of active components. Subsequently the solvent is removed from the filtrate by distillation. In order to increase the concentration of unsaponifiable components the liquid fraction can be hydrogenated once more before a second fractionation.

The after-treatment comprises a deodorization of the oil by heating under low pressure, for instance at 150–230° C. and 100–500 Pa, adding steam. The low temperature is necessary to maintain the active components in the oil. By this treatment unpleasant odours and flavourings are removed, as well as optional residues of solvents or pesticides etc.

According to another aspect the invention also refers to a process for fractionation of a vegetable oil giving one or more solid fractions suitable for confectionary applications a well as a liquid fraction rich in unsaponifiable, biologically active components, wherein an optionally pretreated oil having a melting point of 32–55° C. is mixed with solvent in a ratio of 1:3–7 (w/v), heated to transparency, and then cooled at a rate of 0.1–1.5° C./min and filtrated in one or more steps to a first fractionation temperature of −5 to +10° C., at which temperature one or more precipitated solid fractions suitable for use in confectionary applications have been filtered off giving a filtrate F1, which is characterised in that a) the filtrate F1 is evaporated and the liquid fraction hydrogenated to a melting point of 32–55° C.;

b) the hydrogenated liquid fraction is mixed with solvent in a ratio of 1:3–7 (w/v), heated to transparency and then cooled at a rate of 0.5–1.0° C./min and filtrated in one or more steps to a fractionation temperature of −5 to +10° C., at which temperature a solid fraction is filtered off giving a filtrate HF1;

c) the filtrate HF1 is cooled at a rate of 0.1–1.0° C./min, optionally after mixing with additional solvent to a second fractionation temperature of −30 to −15° C., at which temperature a solid fraction is filtered off giving a filtrate F2;

d) the filtrate F2 is distilled to remove the solvent giving a liquid fraction in which the unsaponifiable, biologically active components have been enriched by at least a factor 4.

According to a preferred process shea butter is fractionated giving one or more solid fractions suitable for confectionary applications as well as a liquid fraction rich in unsaponifiable biologically active components, wherein optionally pretreated shea butter having a melting point of 32–38° C. is mixed with acetone in a ratio of 1:4–6 (w/v), heated to transparency, and then cooled at a rate of 0.1–0.5° C./min and filtrated in one or more steps to a first fractionation temperature of +1 to +8° C., at which temperature one or more solid fractions suitable for use in confectionary applications have been filtered off giving a filtrate F1, which process is characterized in that a) the filtrate F1 optionally is mixed with additional acetone;

b) the filtrate F1 is cooled at a rate of 0.1–1.0° C./min to a second fractionation temperature of −25 to −15° C. at which temperature the precipitated solid fraction is filtered off giving a filtrate F2;

c) the filtrate F2 is distilled to remove the solvent giving a liquid fraction in which the unsaponifiable, biologically active components have been enriched by at least a factor 3.

According to another preferred process rapeseed oil is fractionated giving one or more solid fractions suitable for confectionary applications as well as a liquid fraction rich in unsaponifiable biologically active components, wherein an optionally pretreated rapeseed oil hydrogenated to a melting point of 38–48° C. is mixed with acetone in a ratio of 1:4–6 (w/v), heated to transparency, and then cooled at a rate of 0.1–0.5° C./min and filtrated in one or more steps to a first fractionation temperature of −5 to +10° C., at which temperature one or more solid fractions suitable for use in confectionary applications have been filtered off giving a filtrate F1, which process is characterized in that a) the filtrate F1 optionally is mixed with additional acetone;

b) the filtrate F1 is cooled at a rate of 0.1–1.0° C./min to a second fractionation temperature of −25 to −15° C. at which temperature the precipitated solid fraction is filtered off giving a filtrate F2;

c) the filtrate F2 is distilled to remove the solvent giving a liquid fraction in which the unsaponifiable, biologically active components have been enriched by at least a factor 3.

The invention also refers to a liquid vegetable oil fraction rich in biologically active components which can be obtained by the fractionation process of the invention. The liquid vegetable oil fraction has been enriched by a factor of at least 2.0 in biologically active components comprising:

tocopherols and tocotrienols and dimers and isomers thereof;

sterols, methyl sterols, dimethyl sterols, triterpene alcohols and esters thereof with saturated, monounsaturated or polyunsaturated fatty acids having a hydrocarbon chain length of 6–24 carbon atoms and 0 to 6 double bonds, and esters thereof with cinnamic acid or hydroxy and/or methoxy substituted cinnamic acids;

carotenoids and isomers thereof.

A preferred aspect of the invention is a shea butter fraction which can be obtained by the process of the invention, which comprises 64–85% by weight di- and triglycerides and 15–33% by weight unsaponifiable lipid components. In said shea butter fraction the biologically active components comprise cinnamic esters of triterpene alcohols, 10–25% fatty acid esters of triterpene alcohols, 5–10% squalene and other hydrocarbons, less than 1.0% based on the total weight of the concentrate.

Another preferred aspect of the invention is a liquid rapeseed oil fraction rich in biologically active components which can be obtained by the process of the invention and which contains 1.5 to 5% unsaponifiable components, the rest being tri- and diglycerides.

In the rapeseed oil fraction of the invention the unsaponifiable components comprise at least 2000 ppm of mixed tocopherol isomers in their naturally occurring proportions and not less than 1.3% sterols and sterol esters, the sterol composition being dominated by β-sitosterol, campesterol and brassicasterol in their naturally occurring proportions.

The shea butter fraction of the invention can be used as an ingredient of a cosmetical or pharmaceutical preparation, especially for providing UV-protecting and skin moisturizing properties. The enriched content of UV-B absorbing cinnamic acid esters offers an additive effect when combined with commercial sun screens such as octyl methoxycinnamate. An improved photo protection from the combination of the natural substance with a chemical sun screen or a physical filter in a skin care formulation can be obtained. The triterpene alcohols and phytosterols, which have been enriched in the fraction, have an anti-inflammatory action. These substances also have a stabilising effect on cell membranes, which improves the water binding capacity of the epidermis, giving a desired moisturising effect. The triglyceride oil present in the fraction provides emollience and lubricity.

The rapeseed oil fraction of the invention can also be used as an ingredient of a cosmetical or pharmaceutical preparation, The high content of enriched natural tocopherols results in an excellent oxidation stability to the oil fraction, Oil Stability Index (OSI)>100 hours at 110° C. The tocopherols, as free radical scavengers, also offers a protection of other ingredients in a formulation as well as a biochemical protection of epidermal cells from photodamage. Particularly UV-A protecting properties have been demonstrated by the rapeseed oil fraction. Tocopherols in combination with phytosterols are further known to show membrane stabilising properties resulting in improved water binding capacity of the epidermis. Shown anti-inflammatory properties on surfactant damage skin is also related to the epidermis. An anti-irritant and anti-inflammatory effect on damaged skin can also be attributed to the combination of phytosterols and tocopherols.

EXAMPLES

In the following fractionation examples a refined vegetable oil or a fraction thereof is heated to 70° C. prior to mixing with acetone and subsequently cooled at a rate of 0.5–1.0° C./min under constant stirring. When the temperature has reached the supersaturation limit crystals are formed and filtered off as a solid fraction. Further cooling at the same rate will after filtration give another solid fraction. The filtrate contains a third fraction which is a low-melting liquid fraction.

The solvent is recovered by distillation and the liquid oil fraction is deodorized using steam to give the desired end product.

In the examples the melting point is determined according to AOCS Cc 3–25 (slip melting point), and the iodine value is according to Hanus (IUPAC 2.205(m)).

The enrichment factor E, defined as the ratio between the observed amount of active lipid in the fraction divided by the amount of active lipid in the starting oil:

$$E = \frac{C_{toc}(F)}{C_{toc}(S)}$$

wherein $C_{toc}(F)$ is the amount of said active lipid in the fraction, and $C_{toc}(S)$ is the amount in the starting oil. The enrichment factor can be calculated for all active lipids, such as tocopherols (as above), sterols, triterpene cinnamates etc.

Example 1

Fractionation of rapeseed oil

Refined and bleached low erucic acid rapeseed oil (canola oil, Brassica sp) hydrogenated to a melting point of 40° C. is heated to approximately 70° C. and mixed with acetone in the proportions 100 g oil to 400 ml acetone. The resulting mixture has a temperature of 35° C. This mixture is transferred to a stirred vessel placed in a cooling bath held at 30° C. When the mixture has reached the temperature of 31° C., the cooling is started with a rate of 0.5° C./minute with constant stirring. Crystals start to form when the temperature has reached the supersaturation limit and a first solid fraction is filtered off at 10° C. with a yield of approximately 50%. Further cooling at the same rate to −15° C. gives a second solid fraction after filtering. The filtrate contains a liquid fraction, which is a low-melting liquid enriched in biologically active components. The yield of the second solid fraction is 35% and of the liquid fraction 15%.

The enrichment factor for tocopherols in the liquid fraction was found to be 5.5 and for sterols 2.8 and for the second solid fraction 0.3 (tocopherols) and 0.8 (sterols). This demonstrates clearly the preferential enrichment of the desired biologically active lipids in liquid fraction.

The liquid fraction, a rapeseed oil fraction of the invention, was analysed for its content of biologically active lipids using liquid chromatography for tocopherols and gas chromatography after saponification for the sterols.

The content of various tocopherols were found to be 1671 (317) ppm α-tocopherol, 2780 (490) ppm γ-tocopherol and 74 (13) ppm δ-tocopherol. Values for the starting material are given in brackets.

The major sterols found in the liquid fraction were brassicasterol (13% of total sterols), campesterol (33%) and β-sitosterol (47%) with a total sterol content of 2302 ppm. The corresponding numbers for the starting material were 14% (brassicasterol), 34% (campesterol) and 48% (β-sitosterol) and a total sterol content of 822 ppm.

This example shows that the enrichment process does not alter the relative proportion of the tocopherols or sterols in any significative way.

Example 2

Hydrogenation of different oils

The hydrogenated rapeseed oil used in Example 1 was obtained from 1200 g of a refined and bleached low-erucic acid rapeseed oil which was heated with 1.2 g Nysosel 325 under vacuum to 160° C. in a 2-liter Parr hydrogenation reactor. The reactor was flushed with hydrogen and the stirring rate was adjusted to 650 rpm. The hydrogenation was started according to the dead-end principle using a hydrogen partial pressure of 2 bar and a temperature of 180° C. The hydrogenation was stopped when the iodine value was 63 and the catalyst was filtered off. The melting point was 40° C.

A refined and bleached low-erucic acid rapeseed oil was hydrogenated as stated above using Nysosel 545 as catalyst. The reaction was stopped at an iodine value of 60 corresponding to a melting point of 50–51° C.

Refined and bleached maize (corn) oil was hydrogenated as stated above to an iodine value of 70, corresponding to a melting point of 36–37° C.

Example 3

Fractionation of rapeseed oil

A hydrogenated low erucic acid rapeseed oil with a melting point of 42° C. was fractionated by the procedure described in Example 1 but using 700 ml of acetone to 100 g oil. The cooling rate used was 0.5° C./minute and the final crystallisation temperature was −20° C. The yield of the first solid fraction was 52%, of the second solid fraction 38% and of the liquid fraction 10%. The enrichment factor was found to be 10.0 for tocopherols and 3.3 for sterols in the liquid fraction while the corresponding numbers for the second solid fraction were 0.1 and 0.6. This again shows the preferential enrichment of the desired lipids in the liquid fraction, a rapeseed oil fraction of the invention.

Example 4

Fractionation of rapeseed oil

Low erucic acid rapeseed oil hydrogenated to a melting point of 34° C. according to the method in Example 3 was mixed with acetone in the proportions 100 g to 400 ml solvent. The resulting mixture was cooled from 30° C. to 18° C. at a rate of 0.5° C./min to yield 6% of a first solid fraction which was filtered off. The filtrate was further cooled to −1° C. with a rate of 0.5° C. min to yield a second solid fraction (38%) and a filtrate containing a first liquid fraction (56%).

After evaporation of the solvent this first liquid fraction was further fractionated using acetone as a solvent in the proportions 400 ml solvent to 100 g oil. The fractionation was carried out with a cooling rate of 0.8° C./min to a final temperature of −20° C. The yield of the second liquid fraction was 16% and the enrichment factor for tocopherols was 5.0 and for sterols 2.2. Corresponding values for the third solid fraction were 0.4 and 0.9, showing the preferential solubility of the desired lipids in the liquid fraction.

The tocopherol and sterol content and composition of the liquid fractions of Example 3 and 4 are given in the following

TABLE 1

Table 1. Content of sterols and tocopherols in different fractions of rapeseed oil

|  | Example 3 | | Example 4 | |
| --- | --- | --- | --- | --- |
|  | Starting material | Liquid fraction | Starting material | Liquid fraction |
| α-tocopherol (ppm) | 237 | 2260 | 443 | 2106 |
| γ-tocopherol | 390 | 3990 | 773 | 3933 |
| δ-tocopherol | 15 | 144 | 26 | 134 |
| brassicasterol (% of sterols) | 10 | 13 | 11 | 15 |
| campesterol | 35 | 32 | 36 | 34 |
| β-sitosterol | 47 | 46 | 48 | 47 |
| Total sterols (% of product) | 0.823 | 2.689 | 0.894 | 1.946 |

The distribution and content of sterol esters and free sterols in the rapeseed oil fraction was determined using HPLC with cholesteryl oleate as standard. Total sterol content was determined by GC after saponification (E. Homberg, Fat Science Technology, 89(6), 1987, 215-). Free sterols were calculated from the total sterol and sterol ester values using a mass balance calculation after correction for molecular weight differences. The results are shown in the following Table 2:

TABLE 2

|  | Total sterols, analysed (%) | Sterol esters, analysed (%) | Sterol esters, calc. (%) | Free sterols, calc. (%) |
| --- | --- | --- | --- | --- |
| Rapeseed oil | 0.8 | 0.8 | 0.5 | 0.3 |
| Hydrogenated rapeseed oil | 0.8 | 1.0 | 0.6 | 0.2 |
| Fractionated rapeseed oil, step 1 | 0.9 | 0.95 | 0.6 | 0.3 |
| Fractionated rapeseed oil, step 2 | 2.1 | 1.6 | 1.0 | 1.1 |

This shows that the fractionation in a second step to a second, lower fractionation temperature increases the amount of free and esterified sterols in the product.

Example 5

Fractionation of shea butter

A bleached shea butter (Butyrospermum parkii) having a melting point of 34° C. was first fractionated at +4° C. using a temperature gradient of 0.5° C./minute and an acetone/oil ratio of 5/1 (v/w) to yield a solid fraction and a filtrate containing a first liquid fraction in approximately equal yields. After evaporation of the solvent the first liquid fraction was further fractionated using 400 ml acetone/100 g of oil. The cooling starts at 10° C. and a cooling rate of 0.5° C./minute is used until the temperature reaches −12° C. From there to the final crystallisation temperature of −20° C. a cooling rate of 0.1° C./minute was used. The yield of the second liquid fraction is 18% and the enrichment factor for tocopherols was found to be 3.5 and 5.1 for the triterpene esters of cinnamic acid characteristic for the shea butter.

Example 6

Fractionation of shea butter

Another lot of the Shea butter in Example 5 was fractionated using the procedure described in that example. This time the final crystallisation temperature was −15° C. with a cooling rate of 0.5° C./minute followed by 0.1° C./minute from −12° C. The yield of the final liquid fraction was 26% and the enrichment factor for tocopherols was 2.8 and for triterpene esters 4.7.

Composition of shea butter concentrate

The composition and content of biologically active lipids in the final liquid fractions of the shea butter of Examples 5 and 6 were analysed using chromatographic methods and the results are given in Table 3 below.

Tocopherols and tocotrienols were determined by HPLC according to a modified IUPAC 2.432 method.

A lipid class analysis using HPLC was used to separate and quantify the other constituents in the samples.

Experimental conditions:

Step 1: Nucleosil silica column, 4.6 mm ID, 250 mm length held at 30 C, mobile phase hexane/acetic acid 100/0.8, flow 0.9 ml/min, evaporative light scattering detector. Quantification of hydrocarbons, sterol- and triterpene esters of fatty acids.

Step 2: same column as in step 1 but using UV detector at 273 nm, quantification of cinnamates.

Step 3: silica column as above, mobile phase hexane/diethylester/acetic acid 70/30/0.8. Quantification of diglycerides, free sterols and triterpene alcohols. Triglycerides given as the balance.

Triterpene alcohol cinnamates were determined using HPLC. Experimental conditions: semipreparative Nucleosil silica column 250×10 mm. Mobile phase isooctane/diethylether/acetic acid 100/2/0.8. Refractive index detector. The fraction containing triterpene alcohol esters was collected and the solvent evaporated. The residue was dissolved in the mobile phase and injected on an analytical Nucleosil silica column 4.6×250 mm. Mobile phase isooctane/acetic acid 100/0.8. Quantification using UV detector at 273 nm. Lupeol cinnamate was used as a reference for quantification. The lupeol cinnamate was synthesised from lupeol and cinnamoyl chloride in pyridine/chloroform at 80–100° C. for 4 hours, followed by a cleanup on a silica gel column.

The triterpene fraction from the preparative HPLC was also subjected to a gas chromatographic analysis (experimental conditions: DB-17 HT column, 30 m, 0.25 mm ID, 0.15 μm film thickness, FID detector, helium carrier gas, temperature program 80° C. for 1 min followed by a gradient 80–300° C., 20° C./min and 300–340° C., 5° C./min and finally isothermal 340° C. for 40 min. Detector temperature 340° C., injector programmed 80° C. for 1 minute followed by gradient 80–325° C, 50° C./min.

The triterpene cinnamates were identified using authentic samples of lupeol cinnamate, alpha-amyrin cinnamate and beta-amyrin cinnamate. Parkeol, butyrospermol and ψ-taraxasterol were identified by gas chromatography-mass spectroscopy.

Fatty acid composition after conversion to methyl esters was determined according to AOCS Ce 1–62(m)/IUPAC 2.302.

TABLE 3

Content of tocopherols and sterols in shea butter fractions

|  | Filtrate F1 | Filtrate F2 Example 5 | Filtrate F2 Example 6 |
|---|---|---|---|
| TOCOPHEROL content (ppm in fraction) |  |  |  |
| α-tocopherol | 125 | 85 | 93 |
| γ-tocopherol | 42 | 141 | 110 |
| δ-tocopherol | 10 | 33 | 16 |
| α-tocotrienol | <5 | 22 | 20 |
| γ-tocotrienol | <5 | 20 | 9 |
| δ-tocotrienol | <5 | 14 | <5 |
| LIPID CLASS composition (% of fraction) |  |  |  |
| triterpene cinnamates | 5.8 | 16.7 | 15.4 |
| triterpene acetates and fatty acid esters | 2.5 | 7.3 | 6.6 |
| hydrocarbons and sterol esters | 0.9 | 0.7 | 0.8 |
| triglycerides | 85.7 | 63.0 | 66.4 |
| diglycerides | 4.7 | 12.6 | 10.0 |
| TRITERPENE CINNAMATE composition (% of triterpene cinnamates) |  |  |  |
| α-amyrin cinnamate | 40 | 37 | not analysed |
| β-amyrin cinnamate | 6 | 6 |  |
| lupeol cinnamate | 9 | 8 |  |
| butyrospermol cinnamate | 14 | 16 |  |
| parkeol cinnamate | 5 | 5 |  |
| ψ-taraxasteryl cinnamate | 4 | 5 |  |
| others | 22 | 23 |  |
| FATTY ACID composition of GLYCERIDE fraction (% of glycerides) |  |  |  |
| palmitic acid | 5 | 5 | 6 |
| stearic acid | 27 | 9 | 10 |
| oleic acid | 57 | 68 | 67 |
| linoleic acid | 9 | 14 | 14 |

Example 7

Fractionation of shea butter using different temperature conditions

The fractionation of shea butter was carried out in acetone using a solvent to oil ratio of 4:1. The standard procedure comprises a first fractionation at 4° C. to separate a first solid fraction. The remaining filtrate is further fractionated in a second step using a solvent to oil ratio of 4:1 and a cooling rate of 0.8° C./min from 30° C. to –20° C. This gives a second solid fraction and a final liquid fraction at a yield of 18%, corresponding to a total yield of 9% calculated on the starting material.

Three alternative fractionation techniques were employed. In this case the fractionation is carried out in one step without a separation of a first solid fraction at temperatures above 0° C.

The first profile A comprises a cooling from 30° C. to 4.5 using a cooling rate of 0.7° C./min followed by a cooling from 4.5 to –17° C. with a cooling rate of 0.3° C./min. At –17° C. the slurry was kept isothermal for 10 minutes and finally it was cooled to –20° C. using a gradient of 0.3° C./min.

The second profile B comprises a cooling from 30° C. to 5° C. using a gradient of 1° C./min followed by a slow gradient (0.1° C./min) from 5° C. to 0° C. From 0° C. to –20° C. a faster cooling rate (0.7° C./min) was used.

The third alternative profile C starts with a fast cooling with 1° C./min from 30 to 10° C. followed by a slow cooling between 10 and 7° C. (0.1° C./min). From 7° C. to –15° C. a rapid cooling is employed followed by a slow cooling (0.1° C./min) from –15° C. to –20° C.

TABLE 4

Effect of cooling profile on the enrichment factor

|  | Standard | Profile A | Profile B | Profile C |
|---|---|---|---|---|
| Yield (%) | 9 | 12 | 11 | 11 |
| Tocopherols (ppm) | 315 | 340 | 406 | 468 |
| Triterpene alcohols (%) | 24.0 | 21.6 | 19.3 | 24.0 |
| Enrichment factor tocopherols | 3.8 | 4.0 | 4.7 | 5.4 |
| Enrichment factor triterpene alcohols | 5.1 | 4.9 | 4.4 | 5.5 |

These examples show that high yields of the desired lipids may be achieved using a variety of cooling conditions in one or two steps. Especially favorable results are reached when combinations of rapid cooling cycles (to bring down total processing time) and isothermal or quasi-isothermal (slow cooling rates) are employed. The isothermal or slow cooling rate conditions are required to reach a better separation between the fractions.

Example 8

Fractionation of hydrogenated shea butter

Another lot of the shea butter used in Example 5 was first fractionated at +4° C. using a temperature gradient of 0.5° C./min and an acetone/oil ratio of 5/1 (v/w) to yield a solid fraction suitable for use as a confectionary fat ingredient and a filtrate. The filtrate was evaporated and the remaining liquid fraction was hydrogenated using the procedure described in Example 2 to a melting point of 34° C. The resulting hydrogenated oil was mixed with acetone in a ratio of 4/1 (v/w) and cooled from +30 to –20° C. with a cooling rate of 0.5° C./min. At –20° C. a solid fraction was filtered off and the filtrate recovered. After evaporation of the solvent a final liquid fraction enriched in tocopherols and triterpene alcohol esters was obtained in a yield of 8%. The solid fraction had properties suitable for use as an ingredient in a CBR type of confectionary fat. The liquid fraction contained 803 ppm tocopherols corresponding to an enrichment factor of 9.3 and 31.7% triterpene alcohol esters, corresponding to an enrichment factor of 7.2.

Example 9

Fractionation of different oils

The effect of the melting point of the oil, the fractionation temperature and the composition of the starting raw material on the enrichment of unsaponifiable components, especially tocopherols and sterols, was evaluated by comparing the yields obtained under different conditions.

The different oils and conditions are given in the following Table 5.

TABLE 5

Enrichment of tocopherols and sterols
Effect of raw material oil, melting point and fractionation temperature

| | Hydrogenated rapeseed oil | Hydrogenated rapeseed oil | Hydrogenated rapeseed oil | Hydrogenated rapeseed oil | Hydrogenated rice bran oil | Hydrogenated corn oil |
|---|---|---|---|---|---|---|
| Slip mp (° C.) | 34 | 40 | 34 | 45 | 42 | 36 |
| Fractionation temperature (° C.) | −20 | −20 | −5 | −5 | −20 | −20 |
| Solvent/Oil | 4 | 5 | 4 | 4 | 4 | 4 |
| Temperature gradient (° C.) | .8 | .8 | .8 | .5 | .5 | .5 |
| Yield (%) | 12 | 12 | 39 | 16 | 8 | 16 |
| Tocopherols (ppm) | 4565 | 6520 | 1632 | 3469 | 2100 | 6561 |
| Sterols (%) | 1.82 | 2.73 | 0.99 | 1.93 | 1.28 | 2.39 |
| Enrichment tocopherols | 6.6 | 8.5 | 2.4 | 5.1 | 9.7 | 5.6 |
| Enrichment sterols | 2.5 | 3.5 | 1.4 | 2.9 | Not determined | 3.0 |

The values obtained show that the melting point is important for the proper yield and enrichment of the lipids of interest. The higher the melting point, the higher the enrichment and yield of both sterols and tocopherols. The Table 5 also shows that higher fractionation temperatures can be used with higher melting raw materials with the same yield and enrichment of the desired lipids.

EXAMPLES OF FORMULATIONS

Example 10

Body lotion

A vitamineous body lotion containing the fractionated canola oil of Example 1 or 3 was made by mixing phases A and B at 60–70° C. After homogenisation, pH adjustment and cooling, a smooth, moisturising lotion with anti-irritative and soothering properties was obtained.

| Phase | Ingredient | INCI Name | Conc., % w/w |
|---|---|---|---|
| A | LIPEX 109 | Cottonseed (Gossypium hirsutum) oil | 4 |
| | LIPEX Canola-U | Hydrogenated canola oil | 2 |
| | LIPEX 403 | Hydrogenated palm kernel oil | 2 |
| | Arlamol HD | Isohexadecane | 7 |
| | Eutanol ® G | Octyldodecanol | 3 |
| | Cetyl alcohol | Cetyl alcohol | 1.5 |
| | Distilled monoglyceride | Glycerol stearate | 3 |
| | Eumulgin ® B1 | Ceteareth-12 | 1.5 |
| | Eumulgin ® B2 | Ceteareth-20 | 1 |
| | Stearic acid | Stearic acid | 0.2 |
| B | Glycerol, 99.5% | Glycerin | 3 |
| | Potassium hydroxide (1% in water) | | 3 |
| | Water | Aqua | 68.8 |
| C | Preservatives | | q.s. |
| | Fragrance | | q.s. |

LIPEX is a trade-name of Karlshamns AB, Sweden. Arlamol is a trademark of ICI Surfactants. Eumulgin® and Eutanol® are trademarks of Henkel.
LIPEX Canola-U is a hydrogenated canola oil fraction prepared according to Example 1 or 3.

Example 11

UV-stick

A soft stick with photo-protective, emollient and moisturising properties was made according to the formula below. The ingredients in phase A were melted at 85° C. and poured into phase B held at 30–40° C. After thorough mixing the product was poured into moulds and cooled to room temperature.

| Phase | Ingredient | INCI name | Conc., % w/w |
|---|---|---|---|
| A | LIPEX 408 | Hydrogenated vegetable oil | 35 |
| | LIPEX 403 | Hydrogenated palm kernel oil | 15 |
| | Candelilla wax | Candelilla wax | 6 |
| | Beeswax white | Beeswax | 4 |
| | AKOICE E | Hydrogenated vegetable oil | 7 |
| B | AKOMED R | Caprylic/capric triglycerides | 23 |
| | AKOREX L | Hydrogenated Canola Oil | 4 |
| | LIPEX Shea-U | Shea butter | 4 |
| | Tioveil OP | Titanium dioxide (and) Octyl palmitate | 2 |

LIPEX, AKOICE, AKOMED and AKOREX are trade-names of Karlshamns AB, Sweden. Tioveil is a trade-mark of Tioxide Chemicals Inc., USA.
LIPEX Shea-U is a shea butter fraction prepared according to Example 5 or 6.

BIOLOGICAL TESTS

Test 1. Anti-inflammatory test

The aim of this study was to assess the protective effect of test products on stimulated normal human epidermal keratinocytes (NHEK) by measuring production of cytocines after treatment with irritant stress. The method was based on the evaluation of intracellular IL-α production and secreted IL-8 in human keratinocyte cultures in response to a nonsensitizing contact irritant (croton oil).

Normal human epidermal keratinocytes from new-born foreskin (NHEK) were grown in 25-cm$^2$ culture flasks in complete growth medium (KGM, Bioproducts). The cultures were incubated at 37° C. in a humidified 95% air/5% $CO_2$ atmosphere. Before confluency, NHEK are removed from culture flasks by trypsinisation and plated into 24-well microplates at a concentration of $7.0 \cdot 10^3$ cells per well. Cells are incubated at 37° C. When the cells were 50% confluent, the medium was changed to KGM without hydrocortisone and containing the test products at different non cytotoxic concentrations (pretreatment). Keratinocytes were allowed to grow for an additional 48 h period (until they reached 70–80% confluency) in a 5% $CO_2$-air atmosphere at 37° C. After 48 hours treatment, fresh medium without hydrocortisone ($C_0$ control cultures) or fresh medium without hydrocortisone and containing test products was then added and keratinocytes were exposed to croton oil (20 pg/ml) for 24 hours. Keratinocyte morphology and growth over a 24 h treatment were assessed from each culture as an initial gauge of cytotoxicity. IL-8 concentrations were quantified from the cultures supernatants by Elisa according to the manufacturer's instructions (Immunotech). Culture supernatants were collected and then used directly in Elisas.

To quantify intracellular IL-1α, the supernatants were removed and Triton X-100 solution (0.1% in PBS, Ca and Mg free) was added to each well and incubated for 30 min at room temperature. The lysates were stored at −20° C. and then treated as noted above for the supernatant and assayed for IL-1α. Aliquots of cell lysates were tested for protein content (BioRad Protein assay) as a measure of cytotoxic effect.

The following products were tested at 4 concentrations:

Canola oil fraction, prepared in Example 1: $C_1=0.5$, $C_2=1$, $C_3=2.5$ and $C_4=5$ mg/ml Shea butter fraction, prepared in Example 5: $C_1=0.5$, $C_2=1$, $C_3=2.5$ and $C_4=5$ mg/ml Hydrocortisone 21-hemisuccinate sodium : $C_1=0.1$, $C_2=0.25$, $C_3=0.5$ and $C_4=1$ mg/ml IL-8 production The IL-8 concentrations (pg/ml) in supernatants were corrected by protein contents and the anti-inflammatory activity (%) was calculated. In basal conditions (untreated control cultures), croton oil induced an increase in IL-8 production by approximately 50 times. A consistent reduction was detected in the quantities of this cytokine when the supernatants from Canola oil fraction treated cultures and from Hydrocortisone treated cultures were assayed for the presence of IL-8 suggesting that these two products depressed the inflammatory response induced by croton oil. The Canola oil fraction reduced IL-8 by approximately 24% at $C_1$, $C_2$ and $C_3$. Hydrocortisone reduced IL-8 by approximately 50% at the lowest tested concentration.

In contrast, a synergistic response was detected with the combination of croton oil and Shea butter fraction: IL-8 release increased significantly when NHEK were treated by Shea butter fraction at $C_3$ and $C_4$.

IL-1α production

The intracellular IL-1α concentrations (pg/ml) in lysates were corrected by protein contents and the anti-inflammatory activity (%) was calculated. In basal conditions (untreated control cultures) croton oil stimulated the production and intracellular accumulation of IL-1α. The intra-cellular accumulation of IL-1α was increased by croton oil about 3 times. A consistent reduction was detected in the quantities of this cytokine when cell lysates from Canola oil fraction treated cultures and from Hydrocortisone treated cultures were assayed for the presence of IL-1α. If we considered the protein content in the different groups as identical, the efficiency of the 4 tested concentrations of Canola oil fraction could be considered as equivalent and the anti-inflammatory effect was about 30%. As recorded for IL-8, the anti-inflammatory effect of Hydrocortisone was higher than that observed with Canola oil fraction. Hydrocortisone reduced IL-1α by approximately 60% at the lowest tested concentration.

In contrast to its effect on IL-8 production, Shea oil fraction reduced the inflammatory response induced by croton oil. If we considered the protein content in the different groups as identical, the efficiency of the 4 tested concentrations of Shea oil fraction could be considered as equivalent and the anti-inflammatory was about 25%.

Test 2.

UV radiation test of fractionated rapeseed oil in vitro

The fractionated low-erucic rapeseed oil of Example 1, the canola oil fraction, was tested in vitro for its ability to decrease the damage to cells exposed to free radicals generated by exposure to UV radiation. Normal human dermal fibroblasts were exposed to the test substance at different concentrations 48 hours before UV irradiation. DL-α-tocopheryl acetate was used as a positive control in the study. The UV dose inducing 50% of cell death was determined after the treatment by exposing the cell cultures to UV-A and UV-B radiation at different intensities. It was shown that neither the fractionated rapeseed oil of Example 1 or the DL-α-tocopheryl acetate gave any protection against UV-B radiation. However, a highly protective effect against UV-A radiation was observed for the fractionated canola oil of Example 1. The protective effect of the fractionated rapeseed oil was comparable to that of the reference, DL-α-tocopheryl acetate, up to UV-A doses of 17.3 J/cm2.

It was concluded that the fractionated low-erucic rapeseed oil of example 1 has a significant protective effect against uv-a induced free radicals in vitro.

What is claimed is:

1. A process comprising mixing an optionally pretreated vegetable oil having a melting point of 32–55° C. with a solvent in a ratio of 1:3–7 (w/v), heating to transparency, and then cooling at a rate of 0.1–1.5° C./min to a first fractionation temperature of −5 to +10° C. to form one or more precipitated solid fractions suitable for use in confectionary applications, and filtering in one or more steps to separate a filtrate F1, optionally, mixing the filtrate F1 with an additional solvent;

cooling the filtrate F1 at a rate of 0.1–1.0° C./min to a second fractionation temperature of −30 to −5° C. to form a second precipitated solid fraction, and filtering in one or more steps to separate a filtrate F2;

distilling the filtrate F2 to remove the solvent and form a liquid fraction in which the unsaponifiable, biologically active components are enriched by at least a factor 2.

2. The process according to claim 1, wherein the vegetable oil is selected from the group consisting of shea butter, rapeseed oil, canola oil, olive oil, avocado oil, peanut oil, corn oil, soybean oil, sunflower oil, hybrid sunflower oil, wheat-germ oil, illipe butter, mango kernel oil, shorea butter, sal butter, sesame oil, rice bran oil, safflower oil, linseed oil, palm oil, palm kernel oil, coconut oil, cocoa butter, cottonseed oil, oat oil, oat bran oil, and mixtures of said oils.

3. The process according to claim 1, further comprising catalytically hydrogenating the oil or a liquid fraction thereof to increase the melting point to a value within the range of 32–55° C.

4. The process according to claim 1, wherein the second fractionation temperature is within the range of −30 to −15° C.

5. The process according to claim 1, wherein the solvent is a semipolar solvent.

6. The process according to claim 1, further comprising evaporating the filtrate F1 to form a liquid fraction, hydrogenating the liquid fraction to a melting point of 32–55° C.;

mixing the hydrogenated liquid fraction with a solvent in a ratio of 1:3–7 (w/v), heating to transparency, and then cooling at a rate of 0.5–1.0° C./min to a fractionation temperature of −5 to +10C. to form a further solid fraction, and filtering in one or more steps to separate a filtrate HF1;

cooling the filtrate HF1 at a rate of 0.1–1.0° C./min, optionally after mixing with additional solvent; to a second fractionation temperature of −30 to −15° C. to form a second further solid fraction, and filtering in one or more steps to separate a filtrate F2;

distilling the filtrate F2 to remove the solvent and form a liquid fraction in which the unsaponifiable, biologically active components are enriched by at least a factor 4.

7. A process comprising mixing optionally pretreated shea butter having a melting point of 32–38° C. with acetone in a ratio of 1:4–6 (w/v), heating to transparency, and then cooling at a rate of 0.1–0.5° C./min to a first fractionation temperature of +1 to +8° C. to form one or more precipitated solid fractions suitable for use in confectionary applications, and filtering in one or more steps to separate a filtrate F1, optionally mixing the filtrate F1 with additional acetone;

cooling the filtrate F1 at a rate of 0.1–1.0° C./min to a second fractionation temperature of −25 to −15° C. to form a second precipitated solid fraction, and filtering in one or more steps to separate a filtrate F2;

distilling the filtrate F2 to remove the solvent and form a liquid fraction in which the unsaponifiable, biologically active components have been enriched by at least a factor 3.

8. A process comprising mixing an optionally pretreated rapeseed oil hydrogenated to a melting point of 38–48° C. with acetone in a ratio of 1:4–6 (w/v), heating to transparency, and then cooling at a rate of 0.1–0.5° C./min to a first fraction temperature of −5 to +10° C. to form one or more precipitated solid fractions suitable for use in confectionary applications, and filtering in one or more steps to separate a filtrate F1, optionally mixing the filtrate F1 with additional acetone;

cooling the filtrate F1 at a rate of 0.1–1.0° C./min to a second fractionation temperature of −25 to −5° C. to form a second precipitated solid fraction, and filtering in one or more steps to separate a filtrate F2;

distilling the filtrate F2 to remove the acetone and form a liquid fraction in which the unsaponifiable, biologically active components are enriched by at least a factor 3.

9. A liquid vegetable oil fraction rich in biologically active components obtained by the process of claim 1, wherein the biologically active components comprise:

tocopherols and tocotrienols, dimers thereof and isomers thereof;

sterols, methyl sterols, dimethyl sterols, triterpene alcohols and esters thereof with saturated, monounsaturated or polyunsaturated fatty acids having a hydrocarbon chain length of 6–24 carbon atoms and 0 to 6 double bonds, or acetic acid and esters thereof with cinnamic acid or hydroxy and/or methoxy substituted cinnamic acids;

carotenoids and isomers thereof.

10. A liquid shea butter fraction obtained by the process of claim 1, comprising 64–85% by weight di- and triglycerides and 15–36% by weight unsaponifiable lipid components.

11. The shea butter fraction according to claim 10, wherein the biologically active components comprise 10–25% of cinnamic esters of triterpene alcohols, 5–10% of fatty acid esters of triterpene alcohols, less than 1.0% of squalene and other hydrocarbons, based on the total weight of the fraction.

12. A liquid rapeseed oil fraction obtained by the process of claim 1, comprising 1.5 to 5% unsaponifiable components, and a mixture of tri- and diglycerides as a major component.

13. The rapeseed oil fraction according to claim 12, wherein the unsaponifiable components comprise at least 2000 ppm of mixed tocopherol isomers in a naturally occurring proportion and not less than 1.3% sterols and sterol esters, the sterol composition comprising β-sitosterol, campesterol and brassicasterol in a naturally occurring proportion as a major components.

14. The process for fractionation according to claim 5, wherein the solvent is acetone.

15. A liquid vegetable oil fraction rich in biologically active components obtained by the process of claim 7, wherein the biologically active components comprise:

tocopherols and tocotrienols, dimers thereof and isomers thereof;

sterols, methyl sterols, dimethyl sterols, triterpene alcohols and esters thereof with saturated, monounsaturated or polyunsaturated fatty acids having a hydrocarbon chain length of 6–24 carbon atoms and 0 to 6 double bonds, or acetic acid and esters thereof with cinnamic acid or hydroxy and/or methoxy substituted cinnamic acids;

carotenoids and isomers thereof.

16. A liquid vegetable oil fraction rich in biologically active components obtained by the process of claim 8, wherein the biologically active components comprise:

tocopherols and tocotrienols, dimers thereof and isomers thereof;

sterols, methyl sterols, dimethyl sterols, triterpene alcohols and esters thereof with saturated, monounsaturated or polyunsaturated fatty acids having a hydrocarbon chain length of 6–24 carbon atoms and 0 to 6 double bonds or acetic acid, and esters thereof with cinnamic acid or hydroxy and/or methoxy substituted cinnamic acids;

carotenoids and isomers thereof.

17. A liquid shea butter fraction obtained by the process of claim 7, comprising 64–85% by weight di- and triglycerides and 15–36% by weight unsaponifiable lipid components.

18. The shea butter fraction according to claim 17, wherein the biologically active components comprise 10–25% of cinnamic esters of triterpene alcohols, 5–10% of fatty acid esters of triterpene alcohols, less than 1.0% of squalene and other hydrocarbons, based on the total weight of the fraction.

19. A liquid rapeseed oil fraction obtained by the process of claim 8, comprising 1.5 to 5% unsaponifiable components, and a mixture of tri- and diglycerides as a major component.

20. The rapeseed oil fraction according to claim 19, wherein the unsaponifiable components comprise at least 2000 ppm of mixed tocopherol isomers in a naturally occurring proportion and not less than 1.3% sterols and sterol esters, the sterol comprising a mixture of β-sitosterol, campesterol and brassicasterol in a naturally occurring proportion as a major component.

21. A method comprising applying a composition comprising the shea butter fraction of claim 10 to human skin in an amount effective for UV protection, skin moisturizing, anti-inflammation or a combination thereof.

22. A method comprising applying a composition comprising the shea butter fraction of claim 17 to human skin in an amount effective for UV protection, skin moisturizing, anti-inflammation or a combination thereof.

23. A method comprising applying a composition comprising the rapeseed oil fraction according to claim 12 to human skin in an amount effective for UV-protection, skin moisturizing, anti inflammation or a combination thereof.

24. A method comprising applying a composition comprising the rapeseed oil fraction according to claim 19 to human skin in an amount effective for UV-protection, skin moisturizing, anti-inflammation or a combination thereof.

* * * * *